(12) United States Patent
Brown et al.

(10) Patent No.: US 7,917,203 B2
(45) Date of Patent: Mar. 29, 2011

(54) METHOD AND PROBE FOR MEASURING THE IMPEDANCE OF HUMAN OR ANIMAL BODY TISSUE

(75) Inventors: Brian Hilton Brown, Derbyshire (GB); John Anthony Tidy, Sheffield (GB)

(73) Assignees: The University of Sheffield, South Yorkshire (GB); Sheffield Teaching Hospitals NHS Foundation Trust, Sheffield (GB)

( * ) Notice: Subject to any disclaimer, the term of this patent is extended or adjusted under 35 U.S.C. 154(b) by 0 days.

(21) Appl. No.: 11/916,404

(22) PCT Filed: Jun. 2, 2006

(86) PCT No.: PCT/GB2006/002026
§ 371 (c)(1),
(2), (4) Date: Dec. 3, 2007

(87) PCT Pub. No.: WO2006/129108
PCT Pub. Date: Dec. 7, 2006

(65) Prior Publication Data
US 2009/0024052 A1    Jan. 22, 2009

(30) Foreign Application Priority Data
Jun. 3, 2005    (GB) .................................. 0511289.1

(51) Int. Cl.
*A61B 5/05*    (2006.01)

(52) U.S. Cl. ...................................... 600/547

(58) Field of Classification Search ................... 600/547
See application file for complete search history.

(56) References Cited

U.S. PATENT DOCUMENTS

| 5,184,624 A | | 2/1993 | Brown | |
|---|---|---|---|---|
| 5,630,426 A | * | 5/1997 | Eggers et al. | 600/547 |
| 2003/0105411 A1 | * | 6/2003 | Smallwood et al. | 600/547 |
| 2003/0216661 A1 | * | 11/2003 | Davies | 600/547 |

FOREIGN PATENT DOCUMENTS

| EP | 1078597 | 2/2001 |
|---|---|---|
| WO | WO01/67098 | 9/2001 |

* cited by examiner

*Primary Examiner* — Max Hlndenburg
*Assistant Examiner* — Emily M Lloyd
(74) *Attorney, Agent, or Firm* — Kirton & McConkie; Evan R. Witt

(57) ABSTRACT

A method for determining whether a probe for measuring the impedance of human or animal body tissue has been placed over a boundary between different tissue types is described. The probe used in the method comprises at least a first (16), a second (22), a third (18) and a fourth (20) electrode arranged such that the third (18) and fourth (20) electrodes are each located substantially the same distance from both the first (16) and second (22) electrodes. The method comprises: driving a current between the first (16) and the second (22) electrodes; measuring a first value of an electrical parameter between the third (18) and the fourth (20) electrode; and determining whether the probe has been placed over a boundary between different tissue types based on the first value. A probe for carrying out the method is also described.

6 Claims, 2 Drawing Sheets

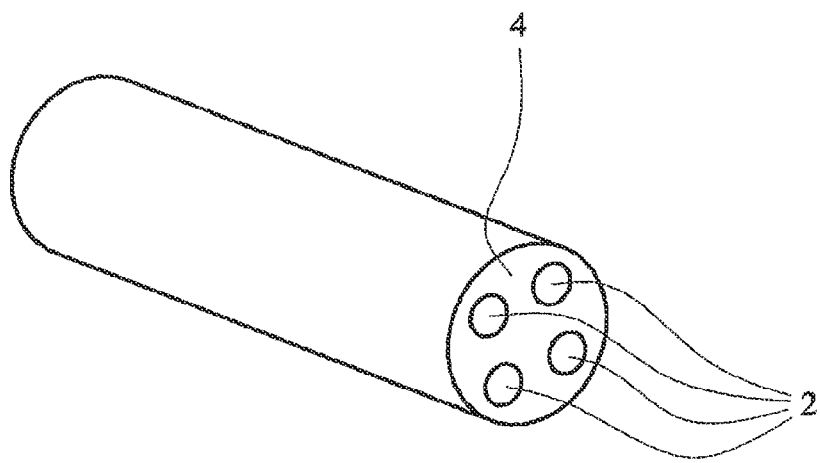
FIG. 1  PRIOR ART
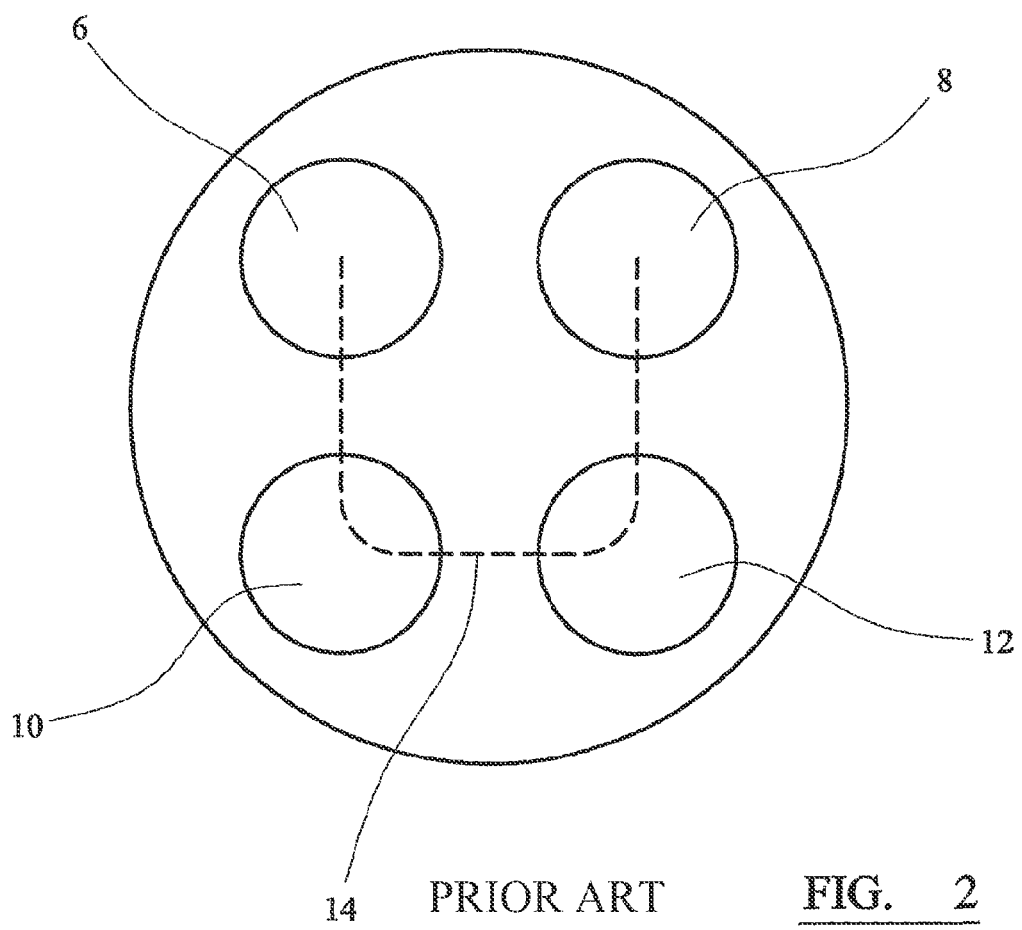
PRIOR ART  FIG. 2

ND AND PROBE FOR MEASURING
METHOD AND PROBE FOR MEASURING THE IMPEDANCE OF HUMAN OR ANIMAL BODY TISSUE

FIELD OF THE INVENTION

The present invention relates to a probe which can measure the impedance of human or animal body tissue. More particularly it relates to a probe which can determine when the probe is placed over a boundary between two different tissue types and a corresponding method.

DESCRIPTION OF RELATED ART

It has been proposed to use measurements of tissue impedance in medical diagnosis applications. An example of a probe suitable for measuring the tissue impedance is discussed in WO-A-01/67098 and is depicted in FIG. 1. The probe comprises four 1 mm diameter gold electrodes 2 which are mounted flush with the end face 4 of the probe and spaced equally on a circle of 1.65 mm radius.

FIG. 2 depicts the way in which the probe is used to calculate a transfer impedance when it has been placed in contact with a tissue to be measured. An ac current $I_1$ of 10 µA peak-to-peak is passed between two adjacent electrodes 6,8 and the real part of the resulting potential $V_1$ between the two remaining electrodes 10,12 is measured. The current path used for measuring the impedance is depicted in FIG. 2 by broken line 14, it runs from electrode 6 to electrode 10 to electrode 12 to electrode 8.

The ratio of the measured potential to the amplitude of the current determines the transfer impedance. Measurements are made at eight frequencies by doubling the frequency in steps between 4.8 kHz and 614 kHz. Measurements may also be made at frequency ranges with an upper limit of up to 1.5 MHz.

The transfer impedance so measured can then be analysed for use in cancer screening because the value will vary according to the type of cells and their arrangements which make up the tissue. The transfer impedance can also be used in screening for pre-term birth.

However, the method can give inaccurate results when the probe is positioned over a tissue boundary. When the probe is used for cervical cancer screening the two major normal tissue types are normal squamous epithelium and columnar tissue. These two tissues are well separated in their impedance spectrums. However, if the probe is placed close to the uterine canal on the border between these two tissue types the resulting measured impedance can look like premalignant tissue. (The impedance spectrum of premalignant tissue lies between that of normal squamous epithelium and columnar tissue.) Therefore, misplacement of the probe may lead to a false positive result.

SUMMARY OF THE INVENTION

It is desirable to reduce the occurrence of false positive results. Accordingly, the present invention provides a method and a probe which can determine whether the probe has been placed over a tissue boundary. Thus an operative can be alerted to reposition the probe slightly to reduce the likelihood of a false positive result.

According to a first aspect of the present invention, there is provided a method for determining whether a probe for measuring the impedance of human or animal body tissue has been placed over a boundary between different tissue types, the probe comprising at least a first, a second, a third and a fourth electrode arranged such that the third and fourth electrodes are each located substantially the same distance from both the first and second electrodes; the method comprising:

driving a current between the first and the second electrode;
   measuring a first value of an electrical parameter between the third and the fourth electrode; and
   determining whether the probe has been placed over a boundary between different tissue types based on the first value.

The electrical parameter may be the potential difference between the third and fourth electrodes, the transfer impedance between the first and second electrodes and the third and fourth electrodes or the current flowing between the third and fourth electrodes. The third and fourth electrodes are each substantially the same distance from the first and second electrodes. Therefore, if the probe has been placed over substantially homogenous tissue the current path through the third electrode will be the same as the current path through the fourth electrode, the system will be balanced and the first value will indicate this.

As the system is balanced the first value can be expected to be low or close to zero. Therefore, in one embodiment, in the step of determining whether the probe has been placed over a boundary between different tissue types, if the first value is not substantially equal to zero it is determined that the probe has been placed over a boundary between different tissue types.

The method can be used with several different arrangements of electrodes, however it is preferred that the first, second, third and fourth electrodes are arranged at the corners of a square with the first and second electrodes diagonally opposite each other. This arrangement is advantageous because it can be used to measure the tissue impedance and also determine whether the apparatus has been placed over a tissue boundary with the same set of four electrodes.

It has also been found that a comparison of the first value with a value of the parameter obtained when measuring the impedance of the tissue is effective at identifying a tissue boundary. Thus, in one preferable embodiment, the step of determining whether the probe has been placed over a boundary between different tissue types comprises:

comparing the first value to a predetermined value, wherein the predetermined value is that expected to be obtained when a current is driven between the first and third electrodes and the electrical parameter is measured between the second and fourth electrode; and wherein if the first value is greater than half the predetermined value it is determined that the probe has been placed over a boundary between different tissue types. More preferably if the first value has a value greater than 20% of the predetermined value it is determined that the probe has been placed over a boundary between different tissue types. Still more preferably, if the first value has a value greater than 10% of the predetermined value it is determined that the probe has been placed over a boundary between different tissue types.

The predetermined value may be provided based on an assumption of a particular tissue type or be an average across all likely tissue types.

In an alternate embodiment, the method may further comprise:

driving the current between the first and third electrodes; and
   measuring a second value of the electrical parameter between the second and fourth electrodes;
   wherein said step of determining whether the probe has been placed over a boundary comprises comparing the first value to the second value and wherein if the first value is greater than half the second value it is determined that the probe has been placed over a boundary between different tissue types. More preferably if the first value has a value greater than 20% of the second value it is determined that the probe has been placed over a boundary between different tissue types. Still more preferably, if the first value has a value greater than 10% of the second value it is determined that the probe has been placed over a boundary between different tissue types.

This method has the advantage that the actual parameter being measured by the probe may be used in the determination of whether the probe is placed over a tissue boundary.

Although unlikely to happen, it is possible that the method above might not detect a tissue boundary which passes between the first and second electrodes or the third and the fourth electrodes because in that case the system will still be balanced. The system will also be balanced if the boundary is parallel to a line drawn between the first and second electrodes or parallel to a line drawn between the third and fourth electrodes. To avoid this problem the method may further comprise rotating the probe slightly, preferably by an angle of less than 45°, and repeating the measurement of the first value of the electrical parameter. A rotation of less than 45° is preferable because of the rotational symmetry of a square electrode arrangement.

In an alternate embodiment, the probe may be provided with more than four electrodes to enable a tissue boundary passing through two of the electrodes to be detected without requiring rotation of the probe.

According to a second aspect of the present invention, there is provided a probe for measuring the impedance of human or animal body tissue, the probe comprising:

at least a first, a second, a third and a fourth electrode arranged such that the third and fourth electrodes are each located substantially the same distance from both the first and second electrodes;

a current source for driving a current between the first and second electrodes;

a measurement circuit for measuring a first value of an electrical parameter between the third and fourth electrodes; and a controller for controlling the current source; and a processor for determining whether the probe has been placed over a boundary between different tissue types based on the first value.

The controller and processor may be implemented in several ways, for example as an application specific integrated circuit (ASIC), a microprocessor, microcontroller or a programmable logic array. The measurement circuit may be a voltmeter or any other circuit which is capable of measuring the potential difference between two points, or an ammeter for measuring the current flowing between two points. In one embodiment the current source, measurement circuit, controller and processor may be integrated into a single integrated circuit.

In one embodiment the processor determines that the probe has been placed over a boundary between different tissue types if the first value is not substantially equal to zero.

Preferably, the first, second, third and fourth electrodes are arranged at the corners of a square with the first and second electrodes diagonally opposite each other. The same electrodes can then be used for impedance measurement and for detecting placement of the probe over a tissue boundary.

In one preferable embodiment, the processor is also for comparing the first value to a predetermined value, wherein the predetermined value is that expected to be obtained when a current is driven between the first and third electrodes and the electrical parameter is measured between the second and fourth electrodes; and wherein if the first value is greater than half the predetermined value it is determined that the probe has been placed over a boundary between different tissue types. More preferably if the first value has a value greater than 20% of the predetermined value the processor determines that the probe has been placed over a boundary between different tissue types. Still more preferably, if the first value has a value greater than 10% of the predetermined value, the processor determines that the probe has been placed over a boundary between different tissue types.

In another preferable embodiment, the current source is also for driving a current between the first and third electrodes; and the measuring circuit is also for measuring a second value of the electrical parameter between the second and fourth electrodes;

wherein the processor determines whether the probe has been placed over a boundary by comparing the first value to the second value, and wherein if the first electrical parameter is greater than half the second value it is determined that the probe has been placed over a boundary between different tissue types. More preferably if the first value has a value greater than 20% of the second value the processor determines that the probe has been placed over a boundary between different tissue types. Still more preferably, if the first value has a value greater than 10% of the second value, the processor determines that the probe has been placed over a boundary between different tissue types.

According to a third aspect of the invention, there is provided a computer program comprising code means that, when executed on a computer system, instructs the computer system to perform the method of the first aspect of the invention. This allows the method of detecting placement of a probe over a tissue boundary to be provided as a retro-fit upgrade. The term computer system is used to encompass both an external computer system connected to the probe and also an internal controller or microprocessor located within the probe which executes instructions to operate the probe.

According to a fourth aspect of the present invention, there is provided a computer program product comprising a computer readable medium bearing a computer program according to the above described third aspect.

BRIEF DESCRIPTION OF THE DRAWINGS

Embodiments of the invention will now be described by way of example only with reference to the accompanying drawings, in which:

FIG. 1 depicts a probe for measuring the impedance of tissue;

FIG. 2 depicts a method for using the probe depicted in FIG. 1 to measure the impedance of tissue;

DETAILED DESCRIPTION

Figure 3:
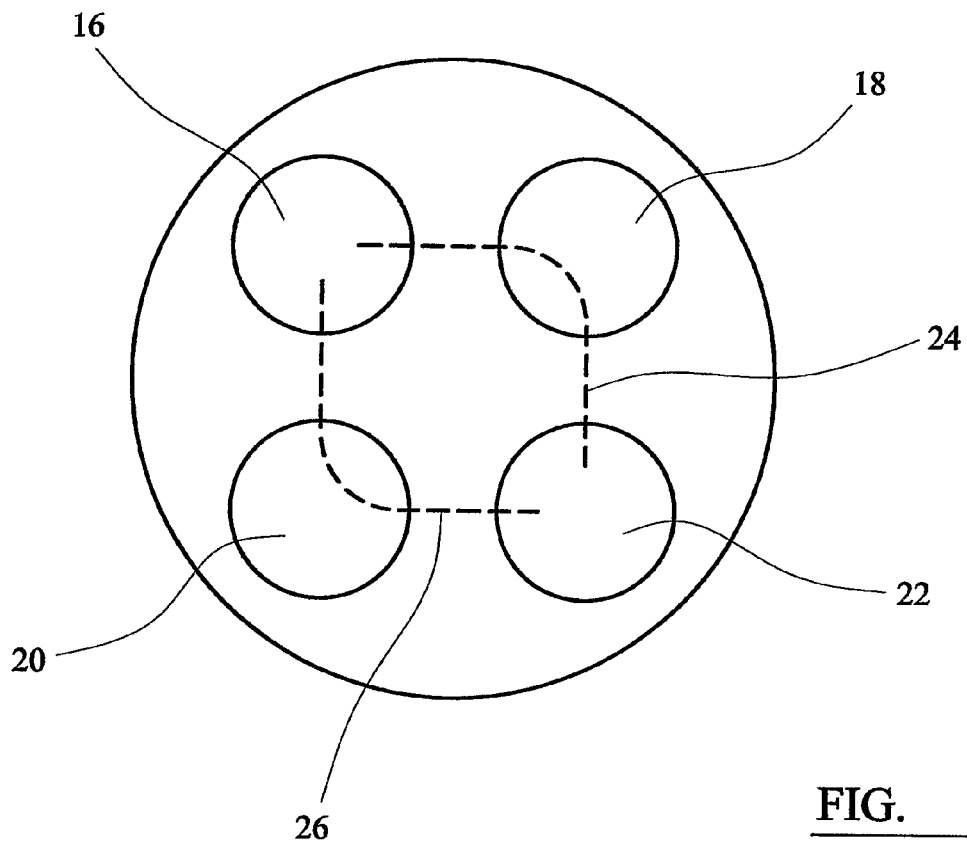
FIG. 3 depicts a method according to the present invention for detecting placement of the probe depicted in FIG. 1 across a tissue boundary.

In a first embodiment, depicted in FIG. 3, a probe is provided with four electrodes 16, 18, 20, 22 are arranged at the corners of a square, as described for example in WO-A-01/

67098. The probe includes a controller and a processor (not shown) which are both implemented by a microprocessor in this embodiment but may also be a microcontroller, an application specific integrated circuit (ASIC), or a programmable logic array. The controller controls the way in which the electrodes are driven.

There are two modes of operation. In the first mode, the probe measures the tissue impedance by driving the electrodes in the same way as that described in WO-A-01/67098. That is, an alternating current supplied from a current source (not shown) is driven between two adjacent electrodes and the resulting potential difference is measured by a measurement circuit (not shown) between the other two electrodes. The ratio of the amplitude of the alternating current to the resulting potential difference can then be used to calculate the tissue impedance. The amplitude of the alternating current may be in the range 1 µA to 1 mA. Measurement is taken at several values in the range of 1 kHz up to an upper limit of 500 kHz to 3 MHz.

In the second mode of operation the electrodes are driven to enable the placement of the probe over a tissue boundary to be detected. The controller controls the current source to drive a current between diagonally opposite electrodes 16, 22 rather than between adjacent electrodes as is the case when measuring tissue impedance. The potential is measured by the measurement circuit between the other two electrodes 18, 20. The same currents and frequencies are used as in the first mode of operation.

This driving arrangement results in two effective current paths which are depicted with broken lines in FIG. 3. The first current path 24 runs from electrode 16 to electrode 22 via electrode 18. The second current path 26 runs from electrode 16 to electrode 22 via electrode 20. By measuring the potential difference across electrodes 18, 20 the probe electrodes now function in a similar way to a bridge circuit. If the tissue on which the probe has been placed is homogenous the effective impedance of path 24 will be the same as the effective impedance of path 26. The geometry of the arrangement is such that the electrodes 18 and 20 are each located the same distance from both electrode 16 and electrode 22. Therefore, in a theoretically ideal situation, the potential measured across electrodes 18 and 20 with homogenous tissue will be substantially equal to zero because the system is balanced.

Figure 4:
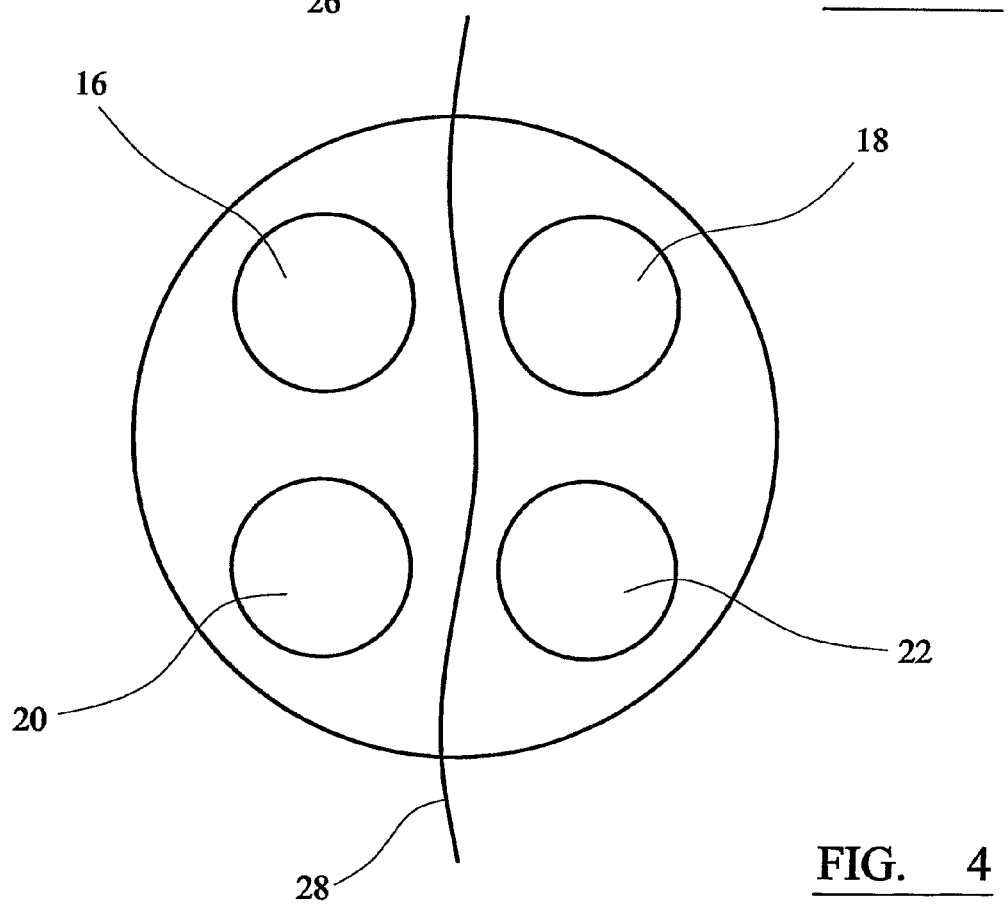
FIG. 4 depicts a probe which has been placed over a tissue boundary.

FIG. 4 depicts the situation in which the probe has been placed over a tissue boundary 28. In this embodiment the probe is used for cervical cancer screening and therefore the two major tissue types are normal squamous epithelium and columnar tissue. These two tissues are well separated in their impedance spectrums. Therefore, when the current is driven between electrodes 16 and 22, the impedance in the path through electrode 18 is not the same as the impedance in the path through electrode 20. As a result a non-zero potential difference will be measured between electrodes 18 and 20, indicating that the probe is placed on a tissue boundary.

The processor determines from the measured potential difference whether the probe has been placed on a tissue boundary. In the event that it is determined that the probe is located on a tissue boundary a visual or audio warning may be communicated to alert the operative to remove the probe. This warning may be transmitted from the probe itself, for example from a light or buzzer in the handle, or from a connected computer system.

The square arrangement of this embodiment has the added benefit that the same electrodes can be used both for tissue impedance measurements and to check that the probe is not located over a tissue boundary. If the probe is located over a tissue boundary any impedance measurements will not be reliable and it is therefore preferable to drive the electrodes to check for a tissue boundary prior to driving them to measure the tissue impedance.

It has been found that the difference between the impedance of tissue types likely to be encountered in cancer screening is most different at lower frequencies. Therefore, the detection of a tissue boundary can be improved by driving the current at generally lower frequencies than those used for tissue impedance measurement.

It is possible that a tissue boundary which passes diagonally under the probe, coincident with either electrodes 16 and 22 or electrodes 18 and 20 will not be detected because the resulting system will still be balanced. Likewise, the system will also be balanced if the tissue boundary is parallel to the line between electrodes 16 and 22 or parallel to the line between electrodes 18 and 20. To avoid lack of detection because of this, the operator may rotate the probe slightly about its central axis before the probe repeats the boundary detection. An angle of rotation of less than 45° is preferred because of the rotational symmetry of the square electrode arrangement.

In a second embodiment of the present invention, which is the same as the first except as described below, the measured value of potential difference obtained when operating the electrodes to detect a tissue boundary is compared with another value to determine the presence of a tissue boundary.

The present inventors have found that if the probe has been placed over a tissue boundary, the potential difference measured between electrodes 18 and 20 when a current is driven between electrodes 16 and 22 (the second mode of operation) is similar to that obtained when a current is driven between electrodes 16 and 18 and a potential measured between electrodes 20 and 22 (the first mode of operation). Therefore, in this embodiment a comparison method is used to detect a tissue boundary. This can give more accurate results because the theoretically ideal situation of a completely balanced system resulting in a zero potential difference may rarely occur in practice.

The potential difference measured between electrodes 16 and 22 in the second mode of operation may be compared to a predetermined value representative of likely values of potential difference obtained when the probe is used for impedance measurement in the first mode of operation. Alternatively, the probe may first be used for impedance measurement, and the tissue boundary detection may make a comparison with the results obtained from operation in the first mode.

If no tissue boundary is present, the value of potential difference measured in the second mode will be less than that of the first mode. The processor determines a tissue boundary is present if the potential difference measured in the second mode is greater than 50% of the value of the predetermined value or the value measured in the first mode. Changing this value can alter the sensitivity to a tissue boundary. In alternate embodiments which are more sensitive to a tissue boundary, it is determined that a tissue boundary is present if the potential difference measured in the second mode is greater than 20%, or alternatively greater than 10% of the predetermined value or the value measured in the first mode.

In an alternate embodiment, the electrodes can be arranged other than in a square, providing that there are first and second electrodes for driving a current between and third and fourth electrodes for measuring a potential difference arranged such that the third and fourth electrodes are each located substantially the same distance from both the first and second electrodes. An example of such an arrangement is where the electrodes are placed at the corners of a kite shape (a quadrilateral which is symmetrical about one diagonal).

In alternate embodiments more than four electrodes can be provided. In these embodiments there must be two electrodes between which a current can be driven between and two electrodes for measuring potential spaced an equal distance from both of the two electrodes through which a current is driven. An example of an arrangement suitable for use with more than four electrodes is a regular hexagon.

All of the above embodiments could be adapted to use the measured potential to calculate the transfer impedance between the electrodes 18 and 20 and the electrodes 16 and 22. This can be calculated from the ratio of the measured potential between electrodes 18 and 20 to the amplitude of the current between electrodes 16 and 22. Likewise, the embodiments can be adapted to measure the current flowing between the electrodes 18 and 20. In these cases, because the system is balanced, the value of the parameter measured will be zero or close to zero in an ideal theoretical situation. The method of comparing the values will also work in the same way as described for potential difference.

The invention claimed is:

1. A method for determining whether a probe has been placed over substantially homogenous tissue, wherein the probe measures the impedance of human or animal body tissue, the probe comprising at least a first, a second, a third and a fourth electrode arranged such that the third and fourth electrodes are each located substantially the same distance from both the first and second electrodes; the method comprising:

driving a current between the first and the second electrode while simultaneously measuring a first value of an electrical parameter between the third and fourth electrode; and determining whether the probe has been placed over substantially homogenous tissue based on the first value or a calculation based on the first value, wherein if the first value or a calculation based on the first value is substantially equal to zero then it is determined that the probe has been placed over substantially homogenous tissue.

2. The method according to claim 1 for use with a probe wherein the first, second, third and fourth electrodes are arranged at the corners of a square with the first and second electrodes diagonally opposite each other.

3. A computer program product comprising a non-transitory computer readable medium bearing a computer program comprising code means that, when executed on a computer system, instructs the computer system to perform the method according to claim 1.

4. A computer program product comprising a non-transitory computer readable medium bearing a computer program comprising code means that, when executed on a computer system, instructs the computer system to perform the method according to claim 2.

5. A probe configured to measure the impedance of human or animal body tissue, the probe comprising:

at least a first, a second, a third, and a fourth electrode arranged such that the third and the fourth electrodes are each located substantially the same distance from both the first and second electrodes;

a current source for driving a current between the first and second electrodes;

a measurement circuit for measuring a first value of an electrical parameter between the third and fourth electrodes simultaneously as the current source drives the current;

a controller for controlling the current source; and a processor for determining whether the probe has been placed over substantially homogenous tissue based on the first value or a calculation based on the first value, wherein the processor determines that the probe has been placed over substantially homogenous tissue if the first value or a calculation based on the first value is substantially equal to zero.

6. The probe according to claim 5, wherein the first, second, third and fourth electrodes are arranged at the corners of a square with the first and second electrodes diagonally opposite each other.

* * * * *